(12) United States Patent
Desmond et al.

(10) Patent No.: US 7,258,776 B2
(45) Date of Patent: Aug. 21, 2007

(54) CAPILLARY ARRAY ASSEMBLY FOR LOADING SAMPLES FROM A DEVICE, AND METHOD

(75) Inventors: Sean M. Desmond, San Carlos, CA (US); John S. Shigeura, deceased, late of Fremont, CA (US); by Janice S. Shigeura, legal representative, Fremont, CA (US)

(73) Assignee: Applera Corporation, Foster City, CA (US)

( * ) Notice: Subject to any disclaimer, the term of this patent is extended or adjusted under 35 U.S.C. 154(b) by 327 days.

(21) Appl. No.: 10/887,477

(22) Filed: Jul. 8, 2004

(65) Prior Publication Data

US 2006/0006068 A1    Jan. 12, 2006

(51) Int. Cl.
*G01N 27/447* (2006.01)
*G01N 27/453* (2006.01)

(52) U.S. Cl. ...................... 204/453; 204/604
(58) Field of Classification Search ........ 206/450–455, 206/600–605
See application file for complete search history.

(56) References Cited

U.S. PATENT DOCUMENTS

| | | | |
|---|---|---|---|
| 5,630,925 A * | 5/1997 | Pentoney et al. ........... 204/604 |
| 6,132,582 A | 10/2000 | King et al. |
| 6,162,341 A | 12/2000 | Nordman et al. |
| 6,372,185 B1 * | 4/2002 | Shumate et al. ............. 422/100 |
| 6,375,817 B1 * | 4/2002 | Taylor et al. ................ 204/453 |
| 6,547,941 B2 * | 4/2003 | Kopf-Sill et al. ........... 204/452 |
| 6,627,446 B1 * | 9/2003 | Roach et al. ................. 436/43 |

OTHER PUBLICATIONS

Notification Concerning Transmittal of Copy of International Preliminary Report on Patentability (Chapter 1 of the Patent Cooperation Treaty) dated Jan. 18, 2007, from PCT Application No. PCT/US05/020763.
International Preliminary Report on Patentability dated Jan. 9, 2007, from PCT Application No. PCT/US05/020763.
Notification of Transmittal dated Nov. 22, 2006, from PCT Application No. PCT/US05/20763.
International Search Report dated Nov. 22, 2006, from PCT Application No. PCT/US05/20763.
Written Opinion of International Searching Authority dated Nov. 22, 2006, from PCT Application No. PCT/US05/20763.

* cited by examiner

*Primary Examiner*—Alex Noguerola
(74) *Attorney, Agent, or Firm*—Kilyk & Bowersox, P.L.L.C.

(57) ABSTRACT

A capillary array assembly is provided that can be used to inject samples into an electrophoresis device. The capillary array assembly can include an injection end that can be arranged to interface with output wells of a fluid processing device, for example, a microfluidic card-type device.

33 Claims, 7 Drawing Sheets

Fig. 1.

PRIOR ART

CAPILLARY ARRAY ASSEMBLY FOR LOADING SAMPLES FROM A DEVICE, AND METHOD

FIELD

The present teachings relate to a capillary arrays assembly for an electrophoresis device that can be capable of separating and analyzing samples, for example, DNA and proteins. More particularly, the present teachings relate to the injection end of a capillary array assembly.

BACKGROUND

Capillary electrophoresis devices are useful for separating and analyzing samples, such as DNA and proteins. There exists a need for a capillary electrophoresis device that is capable of receiving and loading samples from devices, such as microfluidic devices or microfluidic sample containers. In particular, a need exists for a capillary array assembly having an injection end that can interface with the output reservoirs of a microfluidic device.

SUMMARY

According to various embodiments, a device is provided that can include a base, bar, header, or platform, and a plurality of capillary injectors supported thereby. Each capillary injector can include an injection end that extends from the base and includes a distal end. The base can maintain the plurality of capillary injectors arranged in an array that can include at least two spaced-apart sets of capillary injectors. Within each set of capillary, injectors, the capillary injectors can be spaced from one or more adjacent capillary injectors by a first distance, and the two spaced-apart sets of capillary injectors can be spaced-apart from one another by a second distance that is different than the first distance.

According to various embodiments, a device is provided that can include a base and a plurality of capillary injectors as described above, wherein each capillary injector includes a distal injection end and the base can maintain the plurality of distal injection ends arranged in an array that can include two spaced-apart sets of distal injection ends. Within each set of distal injection ends, the distal injection ends can be spaced from one or more adjacent distal injection ends by a first distance, and the two spaced-apart sets of distal injection ends can be spaced-apart from one another by a second distance that can be different from the first distance. According to various embodiments, each distal injection end can include an electrode and a capillary tube.

According to various embodiments, the present teachings provide a system that can include a device including a base and a plurality of capillary injectors as described above, wherein the system can further include a carriage that can be capable of holding the device and a positioning unit that can be capable of moving a sample-containment device into and out of an injection position with respect to the injection array.

According to various embodiments, the present teachings provide a system that can include a device including a base and a plurality of capillary injectors as described above, wherein the system can further include a platform that can be capable of holding the device in an operative position, a carriage that can be capable of holding a microfluidic sample container, and a positioning unit that can be capable of operatively positioning the microfluidic sample container held by the carriage, relative to the device.

According to various embodiments, the present teachings provide a system that can include an injection device including a plurality of capillary injectors each having in injection end. The plurality of injection ends can be arranged in an array. The system can include a microfluidic device comprising a plurality of output reservoirs that can be arranged in an array, and a plurality of pathways. Each pathway can include at least one channel and a respective one of the output reservoirs. The array of injection ends can be complementary to the array of output reservoirs.

The present teachings provide a method that can include providing an injection device having a plurality of capillary injectors, each capillary injector can have an injection end and the plurality of injection ends can be arranged in an array. The method can include providing a microfluidic device comprising a plurality Of output reservoirs arranged in an array and a plurality of pathways, each pathway can include at least one channel and a respective one of the output reservoirs. The method can include moving the injection device relative to the microfluidic de-ice such that each injection end of the array of injection ends can be inserted into a first respective complementary output reservoir of the array of output reservoirs.

It is to be understood that both the foregoing general description and the following detailed description are exemplary and explanatory only and are intended to provide a further explanation of the various and man embodiments described herein.

BRIEF DESCRIPTION OF THE DRAWINGS

Various embodiments of the present teachings are exemplified in the accompanying drawings. The teachings are not limited to the embodiments depicted in the drawings, and include equivalent structures and methods as set forth in the following description and as would be known to those of ordinary skill in the art in views of the present teachings. In the drawings.

DETAILED DESCRIPTION OF CERTAIN EMBODIMENTS

According to various embodiments, a capillary electrophoresis device can be provided that includes a plurality of components, for example, a capillary array component, a sample tray component, a power supply Unit, an optical detection system and the like. According to various embodiments, the capillary electrophoresis device can be used as a DNA analyzer for identifying the respective components of a sample being moved through the capillary array component of the capillary electrophoresis de-ice. The samples can contain, for example, a large number of nucleic acids or nucleic acid sequences that have been labeled with fluorescent dyes, or the like, for identification of different types of nucleotide bases or DNA fragments by way of the optical detection system.

Figure 1:
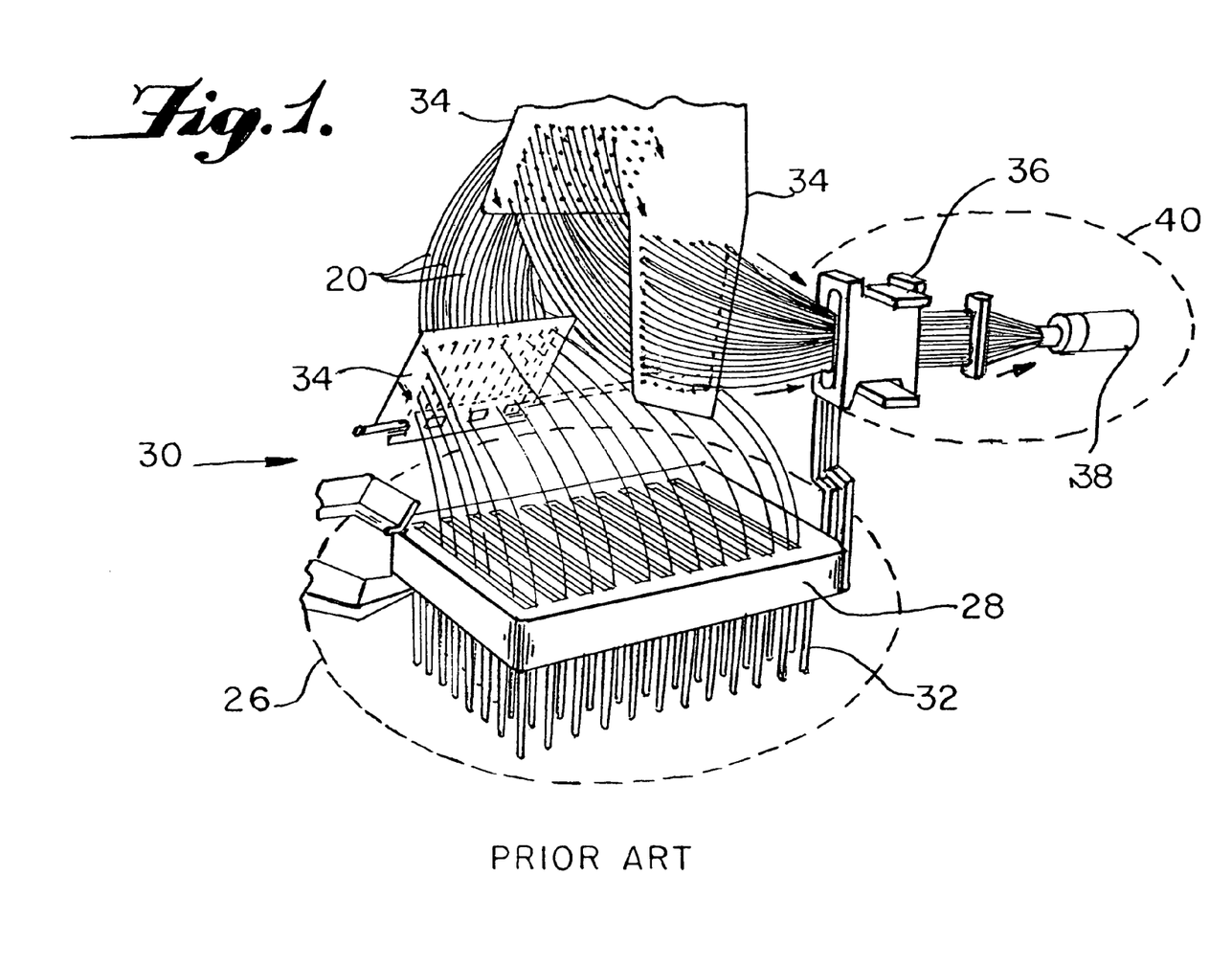
FIG. 1 is a perspective view of a known capillary array assembly.

FIG. 1 illustrates a perspective view of a known capillary array assembly 30 that is capable of being used with a capillary electrophoresis device and a 96 well standard microtiter plate. The capillary array assembly 30 can include a base or header 28, a plurality of hollow capillaries 20, a plurality of capillary support structures 34, a detection cell 36, and a capillary head 38. The capillary array assembly 30 can include an injection end 26 and a detection end 40. A separation medium and a buffer, as a medium for electrophoresis, can be injected into or pre-loaded into the capillaries 20. The capillary, array assembly 30 can be a replaceable member that can be releaseable connected to the capillary electrophoresis device and/or to the detection cell 36. When the capillary array assembly 30 is connected to a capillary electrophoresis device and the ends of each of the hollow capillaries 20, for example, the injecting end portions situated at the injection end 26 of the array, are placed in fluid communication with respective samples to be analyzed, each sample can be, for example, electrokinetically, electroosmotically, electrophoretically, hydrophilically, or hydrodynaimically loaded into a respective capillary of the plurality 20. After sample injection, each of the injecting end portions of the capillaries 20 can be placed in fluid communication with a running buffer and electrophoretic separation of the samples can be performed within each of the capillaries 20. At the end Of its useable lifetime, the capillary array assembly 30 can be detached from the respective capillary electrophoresis device and cleaned, re-loaded, and/or discarded. A new, or the cleaned, capillary array assembly can then be connected to the capillary electrophoresis device.

The known capillary array assembly 30 shown in FIG. 1 is a 96-capillary array arrangement. In the vicinity of the injection end 26 of the 96-capillary array arrangement, the header 28 supports the distal injection ends of each of the capillaries 20 in an organized, evenly-spaced, array. As shown in FIG. 1, a plurality of micro-sized hollow injection electrodes 32 can be arranged to protrude from a surface of the header 28. The injection electrodes 32 are arranged to hold the injection end portions of the capillaries 20 in an organized manner in an array having eight rows and 12 columns. Such a known arrangement of the injection end 26 of the capillary array assembly 30 allows the injection end portions of the capillaries 20 to interface with a standard 96-well receiving well array having correspondingly arranged receiving wells, such as, a 96-well microtiter plate having eight rows and 12 columns of receiving wells. In a known manner, samples arranged in each of the receiving wells can be loaded into each of the capillaries 20 of the capillary array assembly 30 for separation through the capillaries 20 and detection at the detection end 40.

Figure 2:
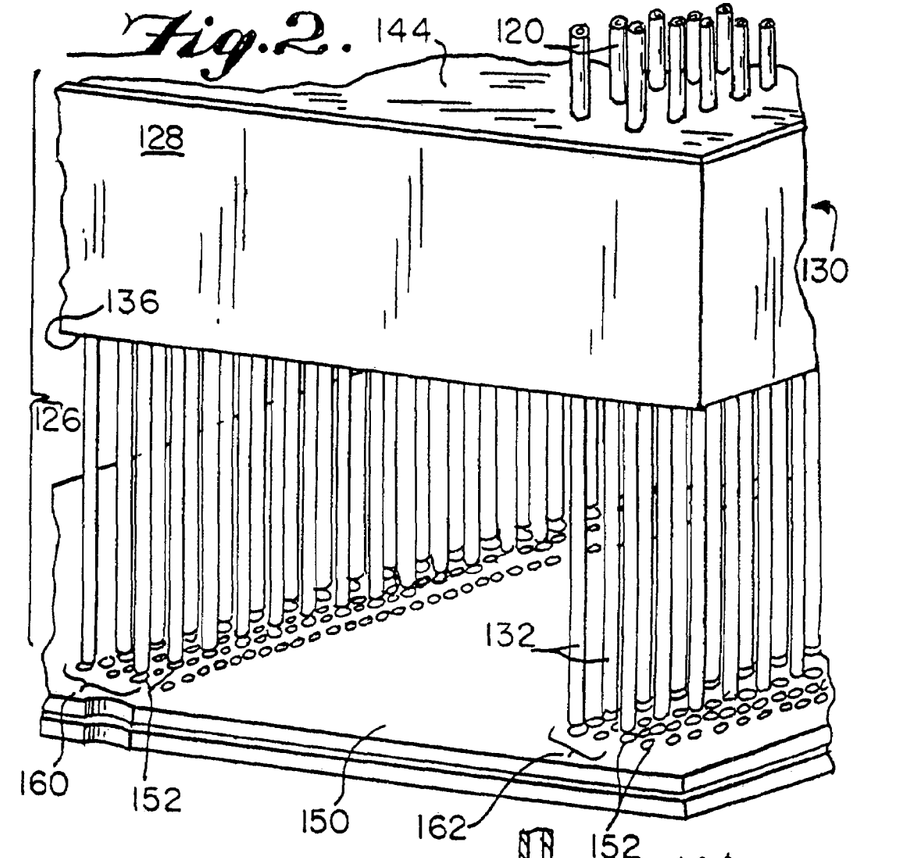
FIG. 2 is a close-up, perspective view of an injection end of a capillary array assembly according to various embodiments, the injection end is shown positioned above the output reservoirs of a device.
Figure 3:
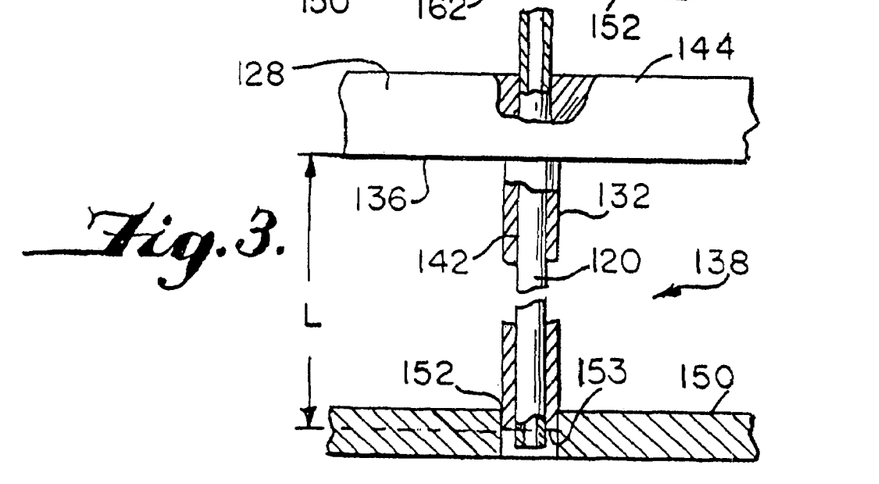
FIG. 3 is a close-up, partial cross-sectional vie of an injection electrode of the distal injection end of the capillary array assembly of FIG. 2, wherein the injection electrode is shown interfacing with an output reservoir of the device.

FIG. 2 shows a perspective, blow-up view of an injection end 126 of a capillary arrays assembly according to various embodiments of the present teachings. The injection end 126 of the capillary array assembly is shown positioned above the output wells 152 of a fluid processing device 150. FIG. 3 shows a close-up, partial cross-sectional view of a portion of the injection end 126 of the capillary array assembly of FIG. 2. FIG. 3 shows a single capillary injector assembly 138, including an injection electrode 132 and a capillary 120, interlacing with a corresponding output ell 152 of the fluid processing device 150.

According, to various embodiments, the fluid processing device 150 can be a microfluidic device or a microfluidic sample container. The microfluidic device or microfluidic sample container 150 can include a plurality of output wells 152 arranged in an array. For example, the fluid processing device 150 can include 4, 8, 16, 24, 32, 48, 96, 192, and 384, or more output wells 152, arranged in an array. According to various embodiments, the output reservoirs can be arranged in any number of possible arrays utilizing varied or uniform spacing, and regular or irregular repeating or non-repeating geometric arrangements. According to various embodiments, the output wells can be arranged in one single array on the device, or in a grouping of arrays. According to various embodiments, the output wells can contain a product from a reaction performed on the fluid processing device 150, or can contain a product of one or more analyses, filtrations, or separations performed on the fluid processing device 150. The microfluidic device or microfluidic sample container 150 can include a plurality of pathways, and each pathways can include at least one channel and a respective one of the output wells 152. Samples can be processed as they pass through the pathways of the fluid processing device 150, and can be ready for further analysis when outputted at the output wells 152. According to various embodiments, in a 192-output well fluid processing device 150, the output wells can have, for example, a diameter of about 2.0 mm and can be about 1.5 mm deep. In a 384-output well fluid processing device 150, the output wells can have, for example, a diameter of about 1.5 mm and can be about 1.5 mm deep.

According to various embodiments, the fluid processing device 150 can be a microfluidic device or a microfluidic simple container, for example, as disclosed in U.S. patent application Ser. No. 10/336,274, filed Jan. 3, 2003, U.S. patent application Ser. No. 10/336,706, filed Jan. 3, 2003, and U.S. patent application Ser. No. 10/336,330, filed Jan. 3, 2003, all of which are incorporated herein in their entireties by reference.

As will be discussed more fully below, the arrangement of the injection end 126 of the capillary array assembly 130, as shown in FIG. 2, including a header 128, injection electrodes 132, capillaries 120, and other disclosed components, allows the injection end 126 to interface with devices having relatively small distances between output reservoirs, as found, for example, in many microfluidic devices, microfluidic card devices, and microfluidic sample containers. The arrangement of the injection end 126 of the capillary array assembly 130 according to various embodiments can allots more than one sample to be efficiently loaded into each of the capillaries 120 of the capillary array assembly 130 from a plurality of relatively densely arranged output wells 152. The arrangement of the injection end 126 of the capillary array assembly according to various embodiments can limit the required relative movement between the injection end 126 and the output reservoir-containing fluid processing device 150 between sample loading operations. As a result, the amount of relative "X" axis and "Y" axis motion required between the injection end 126 of the capillary array assembly and the fluid processing device 150 can be minimized.

Referring to FIG. 2, the injection end 126 of the capillary array assembly according to various embodiments can include a header 128 and a plurality of injection electrodes or injection needles 132, for example, 96 injection electrodes. The injection electrodes 132 can be attached to and/or supported by the header 128. According to various embodiments, the header 128 can connect the injection electrodes 132 to a common electrical system to provide an electrophoresis voltage to the injection electrodes 132 and allow electrokinetic loading of samples. According to various embodiments, the header 128 can include a structure made from a plastic and the injection electrodes 132 can include an electrically conductive material, for example, stainless steel. The electrodes can be formed or provided on the outside of a capillary tube that extends through the electrode.

The injection end 126 can include two, four, or more sets of injection electrodes, for example, each set arranged in two or four routs FIG. 3 shows a partial cross-sectional view through a single capillary injector assembly 138 of the capillary array assembly 130. Each capillary injector assembly 138 can be formed by an injection electrode 132 and a distal injection end portion of a capillary 120. According to various embodiments, the injection electrode 132 of each capillary injector assembly 138 can be formed as a hollow needle. A distal injection end portion of a capillary 120 can be arranged to extend through, and be supported by, at least a portion of the injection electrode 132. As shown in FIG. 3, the distal injection end portion of the capillary 120 can extend all the way through and beyond the tip or injection end 153 of the injection electrode 132. According to various embodiments, the portion of the capillary 120 arranged in the injection electrode 132 can be potted with an epoxy 142 to the injection electrode 132. Each capillary 120 can extend through an injection electrode 132, and through the header 128, and can exit from or extend from a top surface 144 of the header 128. Such and arrangement can allow for the precise alignment of the capillaries 120 in an organized array. FIG. 2 shows a plurality of capillaries 120 passing through the header 128 and exiting from a top surface 144 of the header 128. The capillaries extending from the top surface 144 can be gathered and arranged into a bundle on their paths to the detection end of the capillary array assembly.

According to various embodiments, the injection electrodes 132 can be permanently attached to the header 128. The injection electrodes 132 can be attached to the header 128 by way of an adhesive, by friction fit, or by a capturing device or technique.

As shown in FIG. 3, the injection electrodes 132 can be arranged to extend from a surface 136 of the header 128. Each injection electrode 132 can have a length, L, as measured from the surface 136 of the header 128 to the tip of the injection needle 32. The length, L, of each injection electrode 132 can be about 23.0 mm, or the length, L, can be less than about 23.0 mm The use of shorter injection electrodes 132 can allow easier alignment with the output wells 152 of the device 150 containing the samples to be analyzed. According to various embodiments, the injection electrodes 132 can have a diameter of about 0.71 mm, or less. As discussed above, the output wells 152 of the device 150 can have a diameter, for example, of from about 1.0 mm to about 10.0 mm.

FIG. 2 shows the header 128 of the injection end 126 of the capillary array assembly 130, supporting the plurality of capillary injector assemblies 138 in an organized array. The organized array can have a shape that allows the plurality of capillary injector assemblies 138 to interface with a device having at least the identical number of output reservoirs, or having a number of output reservoirs corresponding to a multiple of the number of capillaries 120 of the capillary array. For example, the capillary array assembly 130 can include a 96-capillary array that can be arranged to interface with a fluid processing device that includes, for example, 96, 192, or 384, output reservoirs. According to various embodiments, the capillary array assemble can include, for example, a 4-capillary array, an 8-capillary array, a 16-capillary array, a 48-capillary array, a 96-capillary array, a 192-capillary array, a 384-capillary array, or the like.

Figure 4:
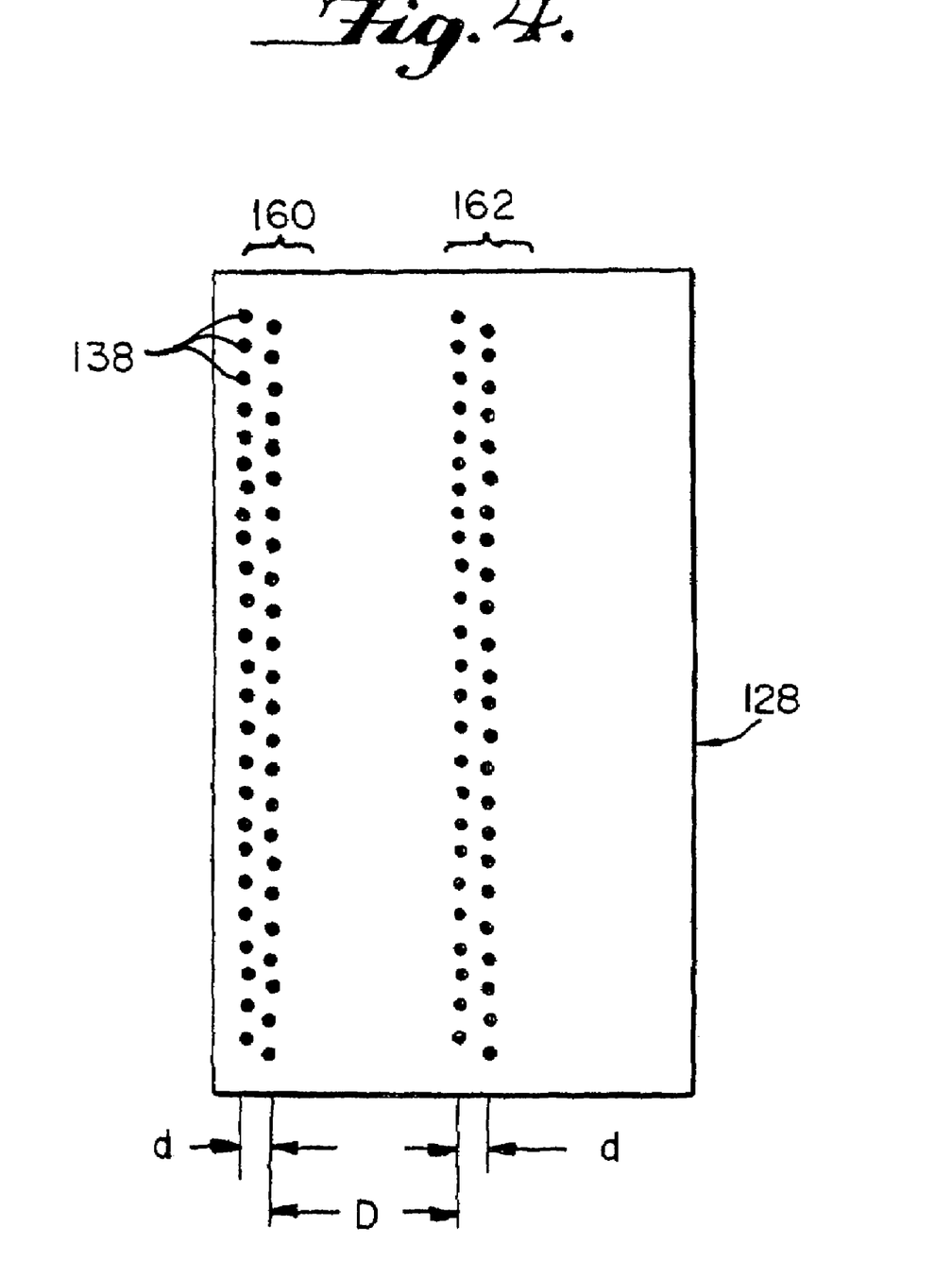
FIG. 4 is a schematic illustration of a cross-section through the base assembly of the injection end of the capillary array assembly according to various embodiments, and shows the positioning of the capillary injector assemblies arranged in an array.
Figure 5:
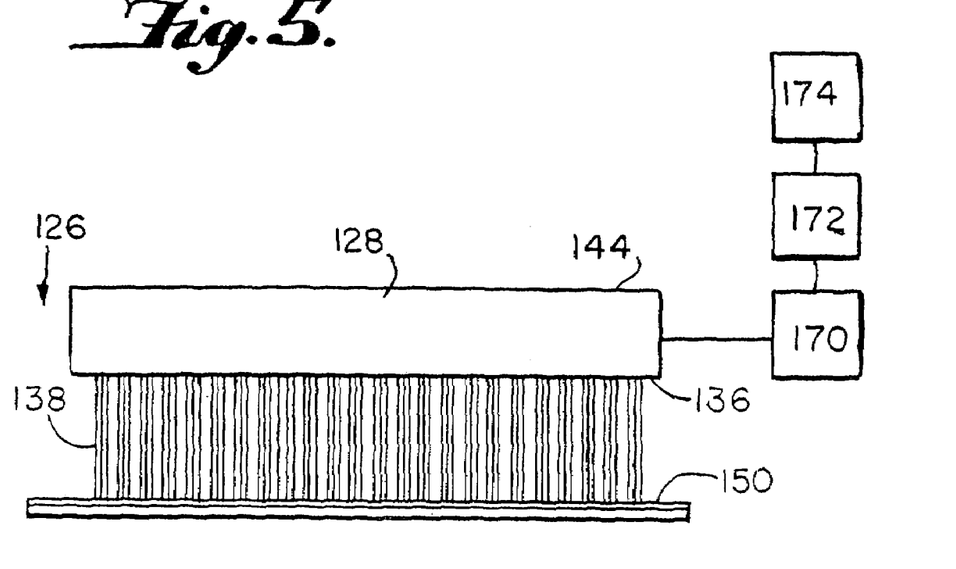
FIG. 5 is a side view of the injection end of the capillary array assembly according to various embodiments, with the injection end shown interfacing with the output reservoirs of a device.
Figure 6:
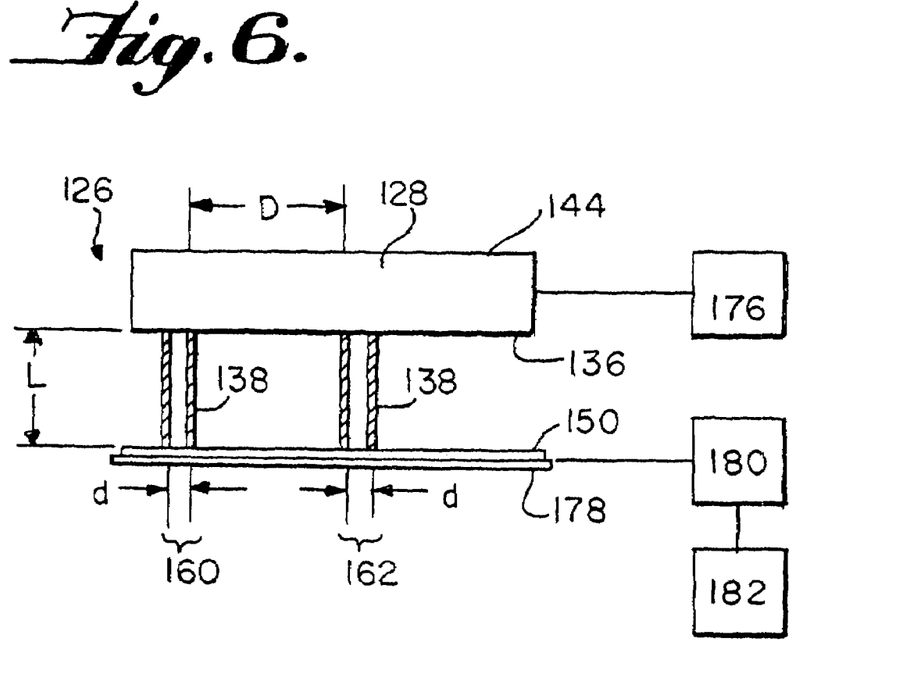
FIG. 6 is an end view of the injection end of the capillary array assembly according to various embodiments, with the injection end shown interfacing with the output reservoirs of the device.
Figure 7:
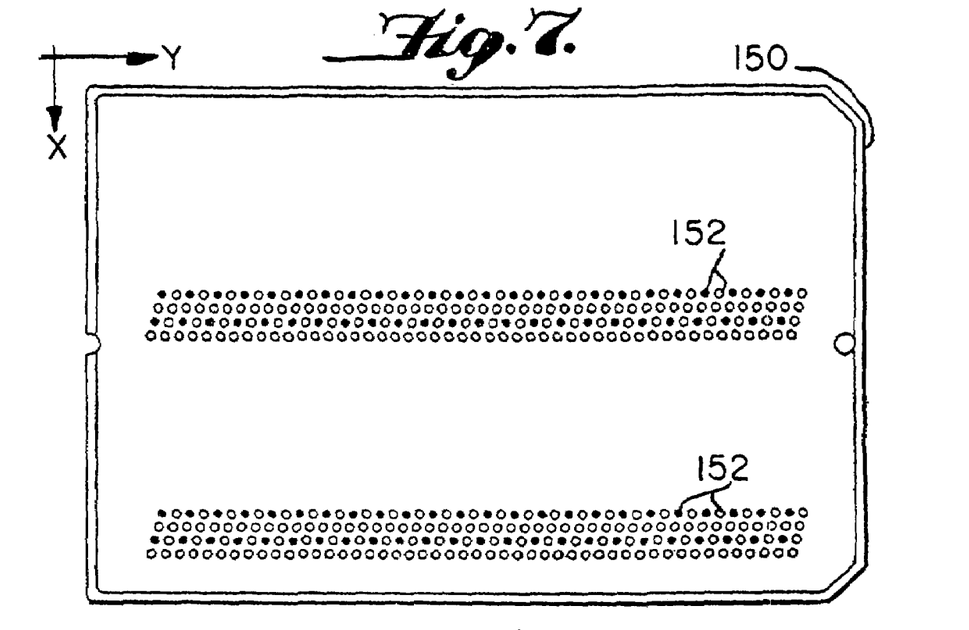
FIGS. 7-10 each show a top view of a device having 384 output reservoirs, the figures sequentially show a possible order that samples can be injected from the output reservoirs of the device into the capillary array assembly according to various embodiments.

According to various embodiments, the header 128 of the injection end 126 can arrange and secure the capillary injector assemblies 138 in an array that can include a plurality of spaced-apart sets of injection assemblies 138. For example. FIG. 4 shows a schematic illustration of a cross-section through the header 128, and shows the positioning of 96 capillary injector assemblies 138 arranged in a 96-capillary array. FIG. 5 shows a side view of the injection end 126 of the capillary array assembly 130 in the process of interfacing with a fluid processing device 150. FIG. 6 shows an end view of the injection end 126 in the process of interfacing with a fluid processing device 150.

As shown in FIGS. 4 and 6, the header 128 can support the 96 capillary injector assemblies 138 in an arrangement including to substantially similarly arranged, spaced-apart sets 160, 162. Each set 160, 162 can include, for example, 48 capillary injector assemblies 138, and each set of 48 capillary injector assemblies can include two rows of 24 capillary injector assemblies 138. As shown in FIGS. 4 and 5, within each set of capillary injector assemblies 138, the first row can be offset with respect to the second row. In each set 160, 162, the capillary injectors 138 can be spaced from one or more adjacent capillary injectors 138 by a first distance, d. The two spaced-apart sets 160, 162 of capillary injector assemblies 138 can be spaced-apart from one another by, a second distance, D, that is different from the first distance, d. The second distance D, can be greater than the first distance, d. For example, the first distance, d, can be from about 3.0 mm to about 6.0 mm, or about 4.50 mm, and the second distance, D, can be from about 20.0 mm to about 40.0 mm, or about 31.50 mm.

Figure 11:
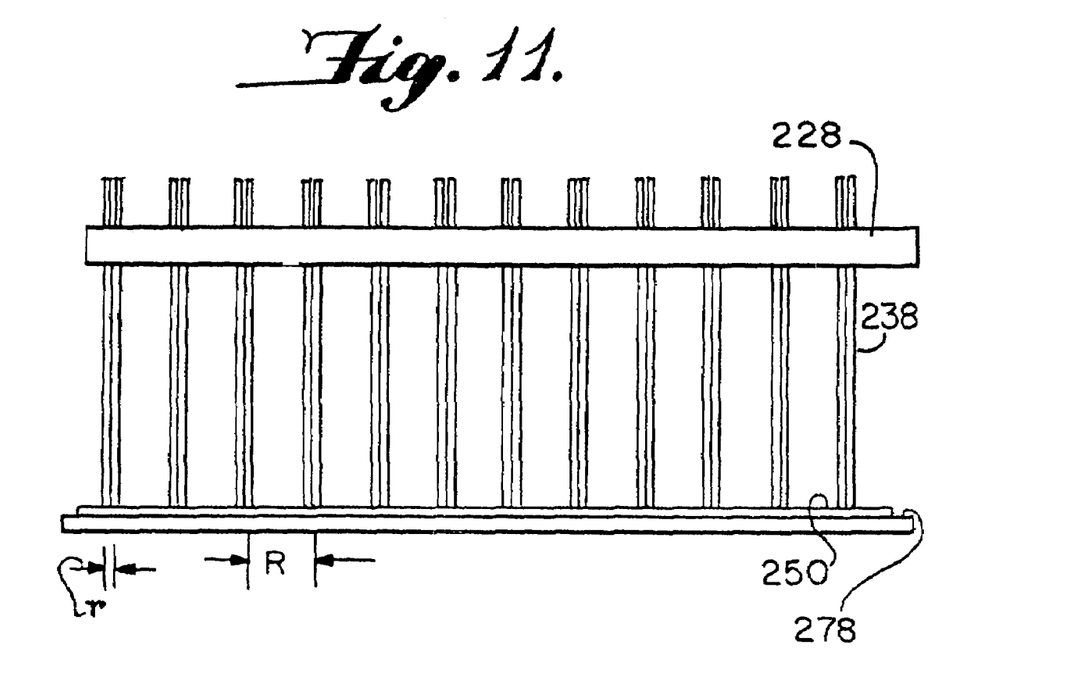
FIG. 11 is a front view of the injection end of the capillary array assembly according to various embodiments, with the injection end shown interfacing with the output reservoirs of a device.
Figure 12:
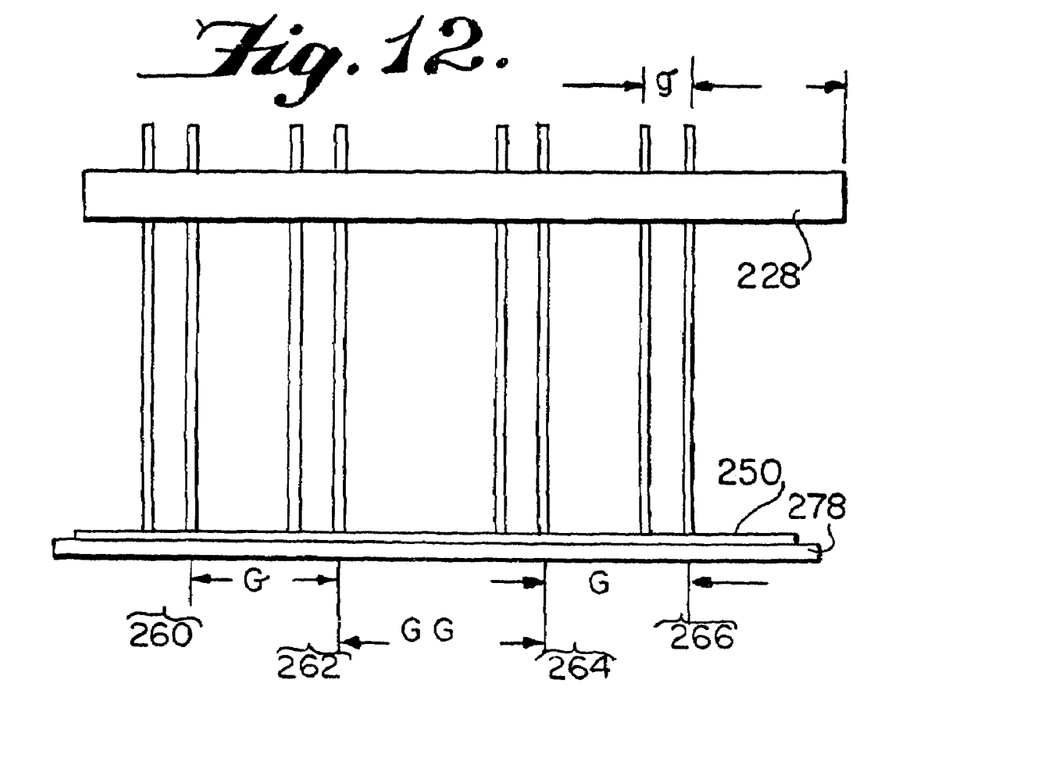
FIG. 12 is a side view of the injection end of a capillary array assembly according to various embodiments, with the injection end shown interfacing with the output reservoirs of a device.

According to various embodiments, the capillary injector assemblies can be arranged in one or more substantially similarly arranged sets of injector assemblies. Each set can include any number of injector assemblies, which can be arranged in one or more rows or columns of injector assemblies. In each set of injector assemblies, the capillary injectors can be spaced-apart from one or more adjacent capillary injectors by a first distance, d. The sets can be spaced-apart from one another by a second distance, D, that is different than the first distance, d. As shown in FIGS. 11 and 12, within a set of capillary injector assemblies, the rows of injectors can be offset from one another.

As shown in FIG. 12, a header 228 can support 96 capillary injector assemblies 238 in an arrangement including four substantially similarly arranged spaced-apart sets 260, 262, 264, 266. Each set 260, 262, 264, 266 can include 24 capillary injector assemblies 238, and each set of 24 capillary injector assemblies can include two rows of 12 capillary injector assemblies 238. As shown in FIG. 11 within each set of capillary injector assemblies 238, the first row can be offset with respect to the second row. In each set 260, 262, 264, 266, the capillary injectors 238 can be spaced from one or more adjacent capillary injectors 238 by a first distance, g. The two spaced-apart sets 260, 262 of capillary injector assemblies 238 can be spaced-apart from one another by a second distance G, that is different from the first distance, g. The second distance. G, can be greater than the first distance, g. For example, the first distance, g, can be about 4.50 mm, and the second distance, G, can be about 15.00 mm. As shown in FIG. 12, the too interior spaced-apart sets, 262, 264 of capillary injector assemblies 238 can be spaced-apart from one another by a third distance, GG, that is different than the second distance G, and different than the first distance g. The third distance, GG, can be greater than the second distance, G. For example, the third distance, GG, can be about 21.00 mm.

According to various embodiments and as shown in FIG. 11, each set 260, 262, 264, 266 of capillary injector assemblies 238 can be in an arrangement including two offset rows of 12 capillary injector assemblies 238. As shown in FIG. 11, the offset between rows can be by a first distance, r. The first distance, r, can be different from the second distance, R, which is the spacing between adjacent capillary injectors 238 in a row of capillary injectors. The second distance, R, can be greater than the first distance, r. For example, the offset distance, r, can be about 1.125 mm, and the second distance, R, can be about 9.00 mm.

According to various embodiments, the detection end of the capillary array assembly can be similar to the detection end of know capillary array assemblies such as the detection end 40 of the capillary array assembly 30 shown in FIG. 1. The capillary array assembly according to various embodiments can be used with existing optics and fluidic assemblies of known capillary electrophoresis devices.

As discussed above, the injection end 126 of the capillary array assembly according to various embodiments can interface With a device 150, such as a microfluidic device, including 48, 96, 192, or 384 output reservoirs, for example. By arranging the capillary injector assemblies 138 in an organized, spaced-apart array arrangement, as shown, for example, in FIGS. 2, 4, 5, and 6, the capillary injector assemblies 138 can interface with a fluid processing device 150 a number of times with a minimum amount of "X" and "Y" axis motion. For example, for a capillary array assembly having 96 capillaries and a fluid processing device 150 having 384 output reservoirs, the capillary injector assemblies 138 can interface with the fluid processing device 150 four different times to conduct electrophoresis on all 384 output reservoirs.

According to various embodiments and as shown in FIG. 5, a carriage 170 can be operatively arranged to hold or secure the header 128. A positioning unit 172 can be operatively arranged with the carriage 170 and can be capable of moving the carriage 170, and in turn, the header 128, into and out of injection positions with respect to the fluid processing device 150. A control unit 174 can be operatively arranged with the positioning unit 172 and can be capable of controlling the positioning unit 172.

According to various embodiments, the fluid processing device 150 can be arranged to move with respect to a substantially stationary injection end 126 of a capillary array assembly. As shown in FIG. 6, a platform 176 can be operable arranged to securely hold the header 128 in an operative stationary position. A carriage 178 can be operatively arranged to hold the fluid processing device 150. A positioning unit 180 can be operatively arranged to be capable of operatively positioning the fluid processing device 150 held by the carriage 178 relative to the stationary injection end 126. A control unit 182 can be operatively arranged with the positioning unit 180 and can be capable of controlling, the positioning unit 180.

By interfacing the capillary injector assemblies 138 of the capillary array assembly with a device 150 in a specific order, the amount of "X" and "Y" axis motion can be minimized. A specific order of interfacing, for example, cam be exemplified by referring to FIGS. 7-10. FIGS. 7-10 each show a top view of a microfluidic device 150 including 384 output wells 152. The microfluidic device 150 can include one or more fluid processing pathways, for example, with a channel reaction site, or one or more other fluid processing feature that is in fluid communication with one or more of the output wells. The microfluidic device 150 can be a card device. The series of figures shown in FIGS. 7-10 represent four consecutive steps by which all 384 samples can be injected from the corresponding 384 output wells 152 of the microfluidic device 150, for example, into a 96-capillary array according to various embodiments described herein. Each figure illustrates which of the output wells 152 of the 384 have been injected into the 96-capillary array by showing those output wells 152 as filled-in dots. Each of FIGS. 7-10 shows the result of injection after one of four sequential moves by the header 128. According to this specific order of interfacing, the header 128 can be designed so that it only needs to move or translate a total of about three mm in the "X" direction and a total of about three mm in the "Y" direction to load samples from all 384 of the output wells 152 of a device 150 having a footprint of about 8.5 cm by 11.0 cm Referring to FIG. 7, the output wells 152 show the result of a first interfacing step performed by the capillary injector assemblies 138 according to the embodiments exemplified in FIGS. 2 and 4-6. Each of the solid-colored output wells 152 represents a well that had contained a sample that has been loaded into a respective capillary injector assembly 138 during the first step. After performing the first interfacing step, the control unit 174 and positioning unit 172 (FIG. 5) can operate to remove the capillary injector assemblies 138 from their first respective positions at the first set of 96 output wells, and translate the header 128 about 2.25 mm along the "Y" axis.

Figure 8:
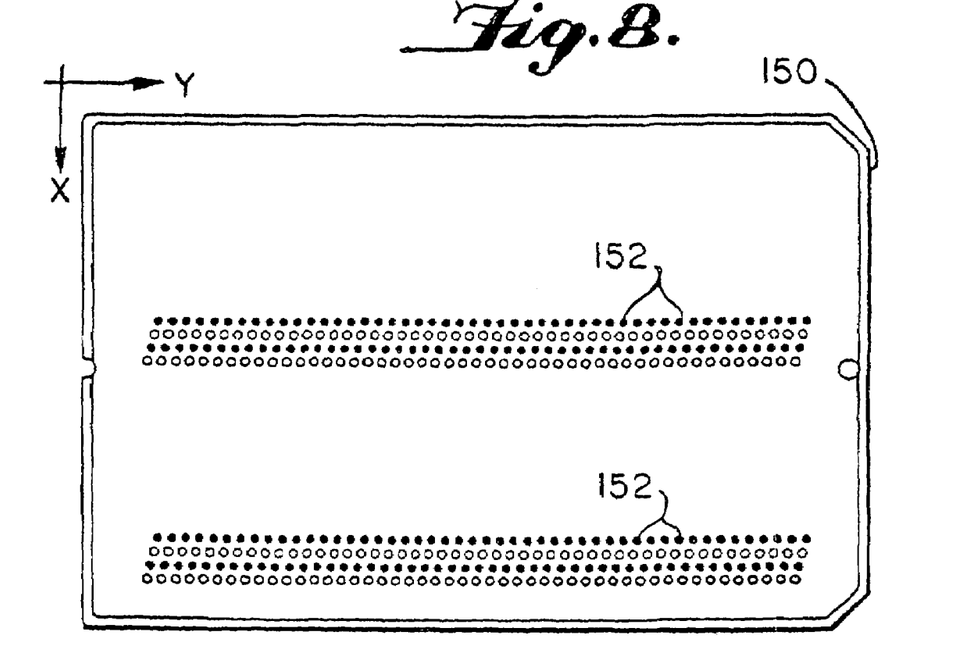
Figure 9:
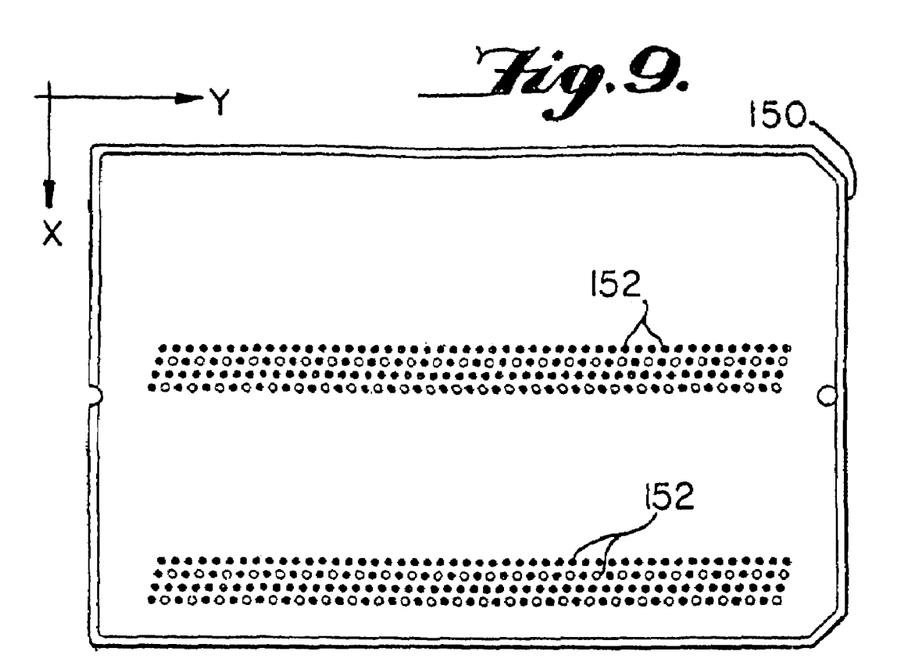

The second interfacing) step is then conducted by moping the capillary injector assemblies 138 into a second set of 96 of the output wells 152 of the microfluidic device 150 and loading samples from the second set of 96 capillaries into the respective capillary injector assemblies 138. The result of such a second step is represented by FIG. 8 that shows an additional 96 solid-colored output wells 152, relative to the 96 shown in FIG. 7. At this point samples from half of the 384 output reservoirs 152 of the device 150 have been loaded.

After performing the second interfacing step, the control unit 174 and positioning unit 172 (FIG. 5) can operate to remove the capillary injector assemblies 138 from the second set of 96 output wells, and can translate the header 128 about 2.25 mm along the "X" axis (from top to bottom) and back about 2.8125 mm along the "Y" axis. The third interfacing step is then conducted by moving the capillary injector assemblies 138 into a third set of output wells 152 of the microfluidic device 150 and loading a third set of 96 samples into the respective capillary injector assemblies 138. The result of such a third step is represented bid FIG. 9 that shows an additional 96 solid-colored output wells 152, relative to the 192 shown in FIG. 8.

Figure 10:
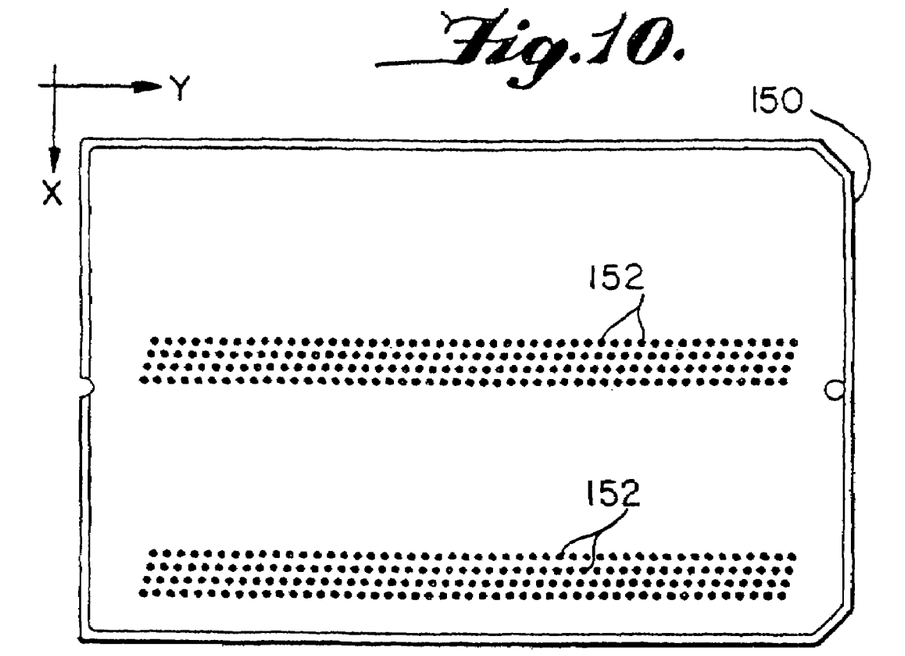

After performing the third interfacing step, the control unit 174 and positioning unit 172 can operate to remove the capillary injector assemblies 138 from the third set of 96 output wells, and can translate the header 128 about 2.25 mm along the "Y" axis to be in position for a fourth interfacing step. The fourth interfacing step is then conducted by moving the capillary injector assemblies 138 into the output reservoirs 152 of the microfluidic device 150 and loading a fourth set of 96 samples respectively into the capillary injector assemblies 138. The result of such a fourth step is represented by FIG. 10 that shows an additional 96 solid-colored output wells 152, relative to the 288 shown in FIG. 9. FIG. 10 shows the result of injecting all 384 samples from all 384 output wells 152 of the microfluidic device 150.

According to various embodiments, the control unit 174 and positioning unit 172 (FIG. 5) can then operate to remove the capillary injector assemblies 138 from the fourth set of 96 output wells. The injecting end portion 126 of the capillary array assembly can be moved into a neutral position after each step, for example, in position for the capillary injector assemblies 138 to be contacted with a running buffer.

According to various embodiments, while FIGS. 7-10 show a possible procedure for loading samples from a fluid processing device into a capillary array assembly, the order in which samples can be loaded can be varied depending, for example, on customer preference, the number of output wells, or other requirements. The injection sequence and positioning unit can be controlled by software or manually.

Other embodiments of the present teachings will be apparent to those skilled in the art from consideration of the present specification and practice of the present teachings disclosed herein. It is intended that the present specification and examples be considered as exemplary only.

What is claimed is:

1. A system comprising an injection device and a capillary electrophoresis device comprising capillaries, wherein the injection device comprises:
    a header; and
    a plurality of capillary injectors supported by the header, each capillary injector comprising a distal injection end that extends away from the header and comprises an electrode and a capillary tube;
    wherein the header maintains the plurality of distal injection ends in an array including a plurality of spaced-apart sets of distal injection ends, within each set of distal injection ends, the plurality of distal injection ends are spaced from one or more adjacent distal injection ends by a first distance, and between each of the plurality of spaced-apart sets of distal injection ends, the sets are spaced-apart from one another by a second distance that is different than the first distance, and the capillary injectors are respectively connected to the capillaries of the capillary electrophoresis device.

2. The system of claim 1, wherein the second distance is greater than the first distance.

3. The system of claim 1, wherein each set of distal injection ends includes at least two rows of distal injection ends.

4. The system of claim 3, wherein each row of distal injection ends includes at least about 8 distal injection ends.

5. The system of claim 3, wherein each row of distal injection ends includes at least about 24 distal injection ends.

6. The system of claim 1, wherein the capillary tube of each distal injection end passes into the electrode.

7. The system of claim 1, wherein each of the distal injection ends is fixed to the header.

8. The system of claim 1, wherein the header includes a first surface, and a second surface opposite the first surface, and the capillary injectors extend though the header and protrude from both the first surface and the second surface.

9. The system of claim 1, wherein the capillaries of the capillary electrophoresis device comprise an array of capillaries, and the capillary injectors are continuous with respective capillaries of the array.

10. The system of claim 1, further comprising:
    a carriage capable of holding the injection device; and
    a positioning unit capable of moving the carriage into and out of a first position.

11. The system of claim 10, further comprising a control unit capable of controlling the positioning unit.

12. The system of claim 1 further, comprising:
    a platform capable of holding the device in an operative position;
    a carnage capable of holding a multi-well fluid sample container in a first position; and
    a positioning unit capable of operatively positioning the carriage relative to the device.

13. The system of claim 12, further comprising a control unit capable of controlling the positioning unit.

14. The system of claim 12, wherein the microfluidic sample container comprises a microfluidic fluid processing device comprising one or more fluid processing pathways.

15. A system comprising:
    an injection device including a plurality of capillary injectors, each capillary injector including an electrode and an injection end, wherein the plurality of injection ends are arranged in an array; and
    a fluid processing device comprising a plurality of output wells arranged in an array, and a plurality of pathways, each pathway including at least one channel in fluid communication with at least one of the output wells;
    wherein the array of injection ends is complementary to the array of output wells.

16. The system of claim 15, wherein the array of output wells includes at least about 96 output wells.

17. The system of claim 15, wherein the array or output wells includes at least about 384 output wells.

18. The system of claim 15, wherein the array of output wells includes at least two times as many output wells as injection ends.

19. The system of claim 18, wherein, within each set of capillary injectors, the plurality of capillary injectors are spaced from one another by a first distance, and the spaced-apart sets of capillary injectors are spaced-apart from one another by a second distance that is greater than the first distance.

20. The system of claim 15, further comprising a carriage capable of holding the injection device, and a positioning unit capable of moving the carriage and operatively positioning the injection device.

21. The system of claim 20, further comprising a control unit capable of controlling positioning of the carriage.

22. The system of claim 21, wherein the control unit is capable of controlling the positioning of the carriage such that the array of injection ends is complementary to the array of output wells in two or more different complementary positions.

23. The system of claim 15, further comprising:
a platform capable of holding the injection device in an operative position;
a carriage capable of holding the fluid processing device; and
a positioning unit capable of operatively positioning the carriage relative to the injection device.

24. The system of claim 23, further comprising a control unit capable of controlling the positioning unit.

25. The system of claim 15, wherein the array of injection ends includes at least two spaced-apart sets of capillary injectors.

26. The system of claim 25, wherein, within each set of capillary injectors, the plurality of capillary injectors are spaced from one another by a first distance, and the at least two spaced-apart sets of capillary injectors are spaced-apart from one another by a second distance that is greater than the first distance.

27. The system of claim 26, wherein each set of capillary injectors includes at least two rows of capillary injectors.

28. The system of claim 27, wherein each row of capillary injectors includes at least 24 capillary injectors.

29. The system of claim 15, wherein the array of injection ends includes at least four spaced-apart sets of capillary injectors.

30. A method comprising:
providing an injection device including a plurality of capillary injectors, each capillary injector including an electrode and an injection end, wherein the plurality of injection ends are arranged in a first array;
providing a fluid processing device comprising a plurality of output wells arranged in a second array, and a plurality of pathways, each pathway including at least one channel in fluid communication with a respective one of the output wells wherein each output well of the plurality of output wells comprises sample disposed therein;
electrokinetically loading the sample from the output wells into the capillary injectors; and
moving the fluid processing device relative to the injection device such that each injection end of the first array is inserted into a first respective output well of the second array.

31. The method of claim 30, further comprising:
moving the fluid processing device relative to the injection device such that each injection end of the first array is removed from a respective complementary output well of the second array and moved into a second respective complementary output well of the second array.

32. The method of claim 30, wherein the fluid processing device is a microfluidic card device.

33. A device comprising:
a header; and
a plurality of capillary injectors supported by the header, each capillary injector comprising a distal injection end that extends away from the header and comprises an electrode and a capillary tube that passes into and through, and extends beyond, the electrode;
wherein the header maintains the plurality of distal injection ends in an array including a plurality of spaced-apart sets of distal injection ends, within each set of distal injection ends, the plurality of distal injection ends are spaced from one or more adjacent distal injection ends by a first distance, and between each of the plurality of spaced-apart sets of distal injection ends, the sets arc spaced-apart from one another by a second distance that is different than the first distance.

* * * * *